US007847091B2

(12) United States Patent
Gleave et al.

(10) Patent No.: US 7,847,091 B2
(45) Date of Patent: Dec. 7, 2010

(54) COMPOSITIONS AND METHODS FOR TREATMENT OF PROSTATE AND OTHER CANCERS

(75) Inventors: Martin E. Gleave, Vancouver (CA); Palma Rocchi, Vancouver (CA); Maxim Signaevsky, Vancouver (CA); Eliana Beraldi, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 12/416,305

(22) Filed: Apr. 1, 2009

(65) Prior Publication Data

US 2009/0221678 A1 Sep. 3, 2009

Related U.S. Application Data

(60) Division of application No. 11/948,195, filed on Nov. 30, 2007, which is a division of application No. 11/422,481, filed on Jun. 6, 2006, now Pat. No. 7,550,580, which is a continuation of application No. 10/605,498, filed on Oct. 2, 2003, now Pat. No. 7,101,991.

(60) Provisional application No. 60/463,952, filed on Apr. 18, 2003, provisional application No. 60/415,859, filed on Oct. 2, 2002.

(51) Int. Cl.
*C07H 21/04* (2006.01)
*C07H 21/02* (2006.01)
*A61K 48/00* (2006.01)

(52) U.S. Cl. .................. 536/24.5; 536/23.1; 536/24.3; 536/24.31; 536/24.33; 514/44

(58) Field of Classification Search .................. None
See application file for complete search history.

(56) References Cited

U.S. PATENT DOCUMENTS

| 5,801,154 | A * | 9/1998 | Baracchini et al. ........ 514/44 A |
| 5,840,708 | A | 11/1998 | Weiss |
| 5,891,858 | A | 4/1999 | Rubenstein |
| 5,962,262 | A | 10/1999 | Hillman et al. |
| 5,998,148 | A | 12/1999 | Bennett et al. |
| 6,905,827 | B2 | 6/2005 | Wohlgemuth et al. |
| 7,250,496 | B2 * | 7/2007 | Bentwich ................... 536/23.1 |
| 2003/0060399 | A1 | 3/2003 | Brophy et al. |
| 2006/0008448 | A1 | 1/2006 | Zu et al. |

FOREIGN PATENT DOCUMENTS

| EP | 0813872 | 12/1997 |
| JP | 09176011 | 7/1997 |
| WO | WO0105435 | 1/2001 |
| WO | WO0170976 | 9/2001 |

OTHER PUBLICATIONS

Richards et al., Effect of overexpression of the small heat shock protein Hsp27 on the heat and drug sensitivities of human testis tumor cells, Cancer Research, May 15, 1996, pp. 2446-2451, vol. 56.
Rondeaux et al., Effects of antisense Hsp27 gene expression in osteosarcoma cells, In Vitro Cell Dev. Biol.-Animal, Oct. 1, 1997, pp. 655-658, vol. 33.
Tamm et al., Antisense therapy in oncology: new hope for an old idea?, Lancet, Aug. 11, 2001, pp. 489-497, vol. 358, No. 9280.
Taylor et al., Antisense oligonucleotides: a systematic high-throughput approach to target validation and gene function determination, Dec. 1999, DDT, pp. 562-567, vol. 4, No. 12.
Wu et al., Expression of the 25-kDa heat-shock protein (Hsp27) correlates with resistance to the toxicity of cadmium chloride, mercuric chloride, cis-platinum(II)-diammine dichloride, or sodium arsenite in mouse embryonic stem cells transfected with sense or antisense Hsp27 cDNA, Toxicology and Applied Pharmacology, Jul. 18, 1996, pp. 330-339, vol. 141.
Yamamoto et al., Heat shock protein 27 was up-regulated in cisplatin resistant human ovarian tumor cell line and associated with the cisplatin resistance, Cancer Letters, Apr. 2, 2001, pp. 173-181, vol. 168.
Bertrand et al., Comparison of antisense oligonucleotides and siRNAs in cell culture and in vivo, Biochemical and Biophysical Research Communications, 2002, pp. 1000-1004, 296.
Dudek et al., Trod: T7 RNAi Oligo Designer, Nucleic Acids Research, 2004, Nucleic Acids Research, vol. 32, pp. W121-W123.
Tuschl et al., The siRNA user guide, Max Planck Institute for Biophysical Chemistry, Aug. 26, 2001 (on-line), retrieved Jan. 31, 2002, pp. 1,3 and 5, http://www.mpibpc.gwdg.de/abteilungen/100/102/siRNAuserguide.pdf.
Stein, The experimental use of antisense oligonucleotides: a guide for the perplexed, The Journal of Clinical Investigation, 2001, pp. 641-644, vol. 108, No. 5.
Aldrian et al., Overexpression of Hsp27 affects the metastatic phenotype of human melanoma cells in vitro, Cell Stress & Chaperones, 2002, pp. 177-185, vol. 7, No. 2.

(Continued)

*Primary Examiner*—Amy Bowman
(74) *Attorney, Agent, or Firm*—Larson & Anderson, LLC

(57) ABSTRACT

Therapeutic agents which target heat shock protein (hsp) 27 in vivo are used to provide treatment to individuals, particularly human individuals, suffering from prostate cancer and other cancers that overexpress hsp27. A therapeutic agent, for example an antisense oligonucleotide or RNAi nucleotide inhibitor with sequence specificity for hsp27 mRNA, for example human hsp27 mRNA, is administered to an individual suffering from prostate cancer or some other cancer expressing elevated levels of hsp 27 in a therapeutically effective amount. The therapeutic agent is suitably formulated into a pharmaceutical composition which includes a pharmaceutically acceptable carrier, and packaged in dosage unit form. A preferred dosage unit form is an injectable dosage unit form.

18 Claims, 10 Drawing Sheets

OTHER PUBLICATIONS

Bubendorf et al., Hormone therapy failure in human prostate cancer: Analysis by complementary DNA and tissue microarrays, Journal of the National Cancer Institute, Oct. 20, 1999, pp. 1758-1764, vol. 91, No. 20.

Cornford et al., Heat shock protein expression independently predicts clinical outcome in prostate cancer, Cancer Research, Dec. 15, 2000, pp. 7099-7105, vol. 60.

Database WPI, Section Ch, Week 199737, 1997, Publisher: Derwent Publications Ltd., London, GB. XP002272450.

Garrido et al, Inconstant association between 27-kDa heat-shock protein (Hsp27) content and doxorubicin resistance in human colon cancer cells: The doxorubicin-protecting effect of Hsp27, European Journal of Biochemistry, 1996, pp. 653-659, vol. 237, No. 3.

Gotham et al., Antisense and SiRNA technologies- SMi Conference, IDrugs, 2003, pp. 211-214, vol. 6, No. 3.

Hargis et al., Antisense Hsp27 oligonucleotides sensitize low pH adapted mammalian cells to hyperthermia, Mar. 2001, Proceedings of the American Association for Cancer Research Annual Meeting, vol. 42, pp. 728-729.

Horman et al., Anti-sense inhibition of small-heat-shock-protein (Hsp27) expression in MCF-7 mammary-carcinoma cells induces their spontaneous acquisition of a secretory phenotype, Mar. 17, 1999, International Journal of Cancer, pp. 574-582, vol. 82.

Jakubowicz-Gil et al., Quercetin, apoptosis, heat shock, Biochemical Pharmacology, 2002, pp. 1591-1595, vol. 64.

Lee et al., The protective role of HSP90 against 3-hydroxykynurenine-induced neuronal apoptosis, Biochemical and Biophysical Research Communications, Jun. 2001, pp. 261-267, vol. 284, No. 2.

Linder et al., Molecular characterization of a novel, developmentally regulated small embryonic chaperone from *Caenorhabditis elegans*, The Journal of Biological Chemistry, Nov. 22, 1996, pp. 30158-30166, vol. 271, No. 47.

Morino et al, Specific regulation of HSPs in human tumor cell lines by flavonoids; in vivo—International Journal of In Vivo Research, 1997, pp. 265-270, vol. 11, No. 3.

Oesterreich et al., The small heat shock protein Hsp27 is correlated with growth and drug resistance in human breast cancer cell lines, Cancer Research, Oct. 1, 1993, pp. 4443-4448, vol. 53.

\* cited by examiner

OD Hsp27/OD Vinculin (% of control)

Effect of Hsp 27 RNAi on the Growth of LN Cap cells in vitro; crystal violet assay

\* $P<0.01$

1x10\*4 cell/ well; cultured in 12-well plate
Hsp 27 RNAi 1nM transfected

% Alive cell ; 3days after transfection of Hsp 27 RNAi to PC3 cells

COMPOSITIONS AND METHODS FOR TREATMENT OF PROSTATE AND OTHER CANCERS

CROSS REFERENCE TO RELATED APPLICATIONS

This application claims the benefit of U.S. Provisional Applications Nos. 60/415,859 filed Oct. 2, 2002 and 60/463,952 filed Apr. 18, 2003, both of which are incorporated herein by reference.

BACKGROUND OF INVENTION

This application relates to compositions and methods for the treatment of prostate and other cancers that express elevated levels of hsp 27 as compared to normal tissue in at least some stages of disease development.

Prostate cancer is the most common cancer that affects men, and the second leading cause of cancer deaths in men in the Western world. Because prostate cancer is an androgen-sensitive tumor, androgen withdrawal, for example via castration, is utilized in some therapeutic regimens for patients with advanced prostate cancer. Androgen withdrawal leads to extensive apoptosis in the prostate tumor, and hence to a regression of the disease. However, castration-induced apoptosis is not complete, and a progression of surviving tumor cells to androgen-independence ultimately occurs. This progression is the main obstacle to improving survival and quality of life, and efforts have therefore been made to target androgen-independent cells. These efforts have focused on non-hormonal therapies targeted against androgen-independent tumor cells (Yagoda et al., *Cancer* 71 (Supp. 3): 1098-1109 (1993); Oh et al., *J. Urol.* 60: 1220-1229 (1998)), however, so far no non-hormonal agent has improved survival. Alternative approaches are therefore indicated.

It has been observed that numerous proteins are expressed in increased amounts by prostate tumor cells following androgen withdrawal. At least some of these proteins are assumed to be associated with the observed apoptotic cell death which is observed upon androgen withdrawal. (Raffo et al., *Cancer Res.*: 4448-4445 (1995): Krajewska et al., *Am. J. Pathol.* 148: 1567-1576 (1996); McDonnell et al., *Cancer Res.* 52: 6940-6944 (1992)).

SUMMARY OF INVENTION

The present invention makes use of therapeutic agents which target heat shock protein (hsp) 27 in vivo to provide treatment to individuals, particularly human individuals, suffering from prostate cancer and other cancers that overexpress hsp27. In accordance with the invention, a therapeutic agent, for example an antisense oligonucleotide or RNAi nucleotide inhibitor with sequence specificity for hsp27 mRNA, for example human hsp27 mRNA, is administered to an individual suffering from prostate cancer or some other cancer expressing elevated levels of hsp 27 in a therapeutically effective amount. The therapeutic agent is suitably formulated into a pharmaceutical composition which includes a pharmaceutically acceptable carrier, and packaged in dosage unit form. A preferred dosage unit form is an injectable dosage unit form.

DETAILED DESCRIPTION

Figure 1A:
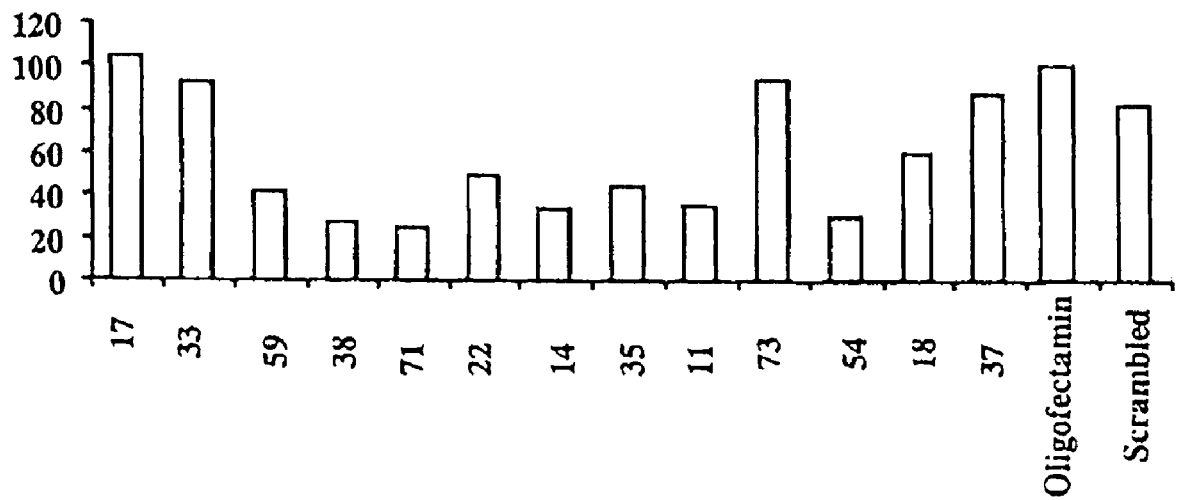
FIGS. 1 A-G show results of mRNA expression tests in cells exposed to antisense oligonucleotides of Seq. ID Nos. 1-81.
Figure 1B:
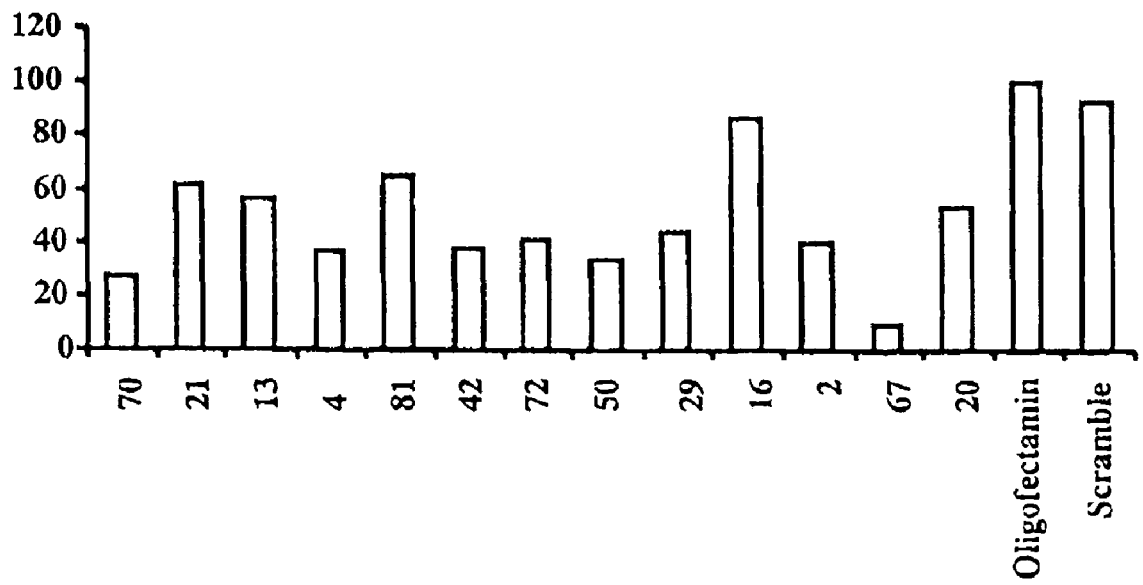
Figure 1C:
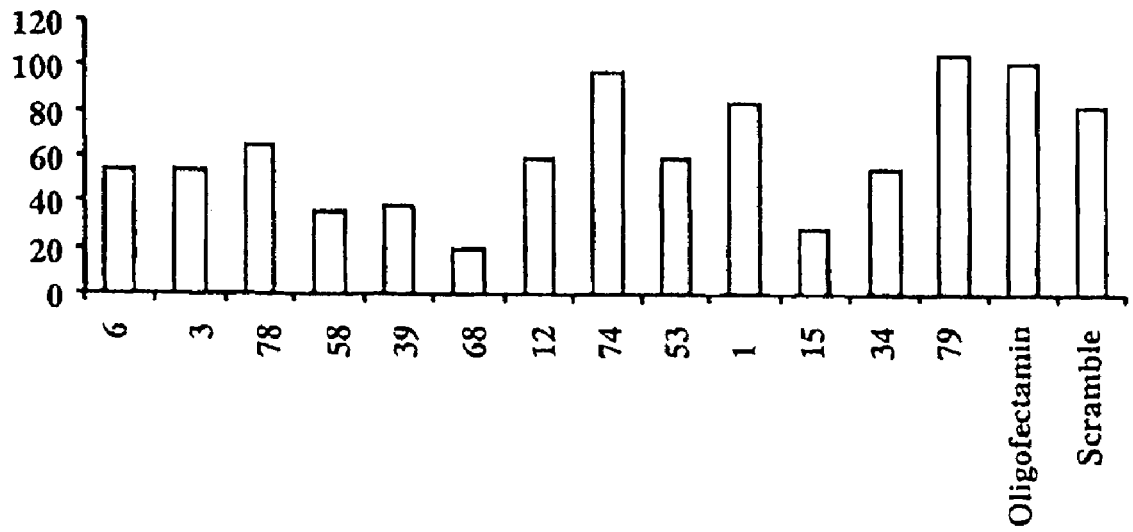
Figure 1D:
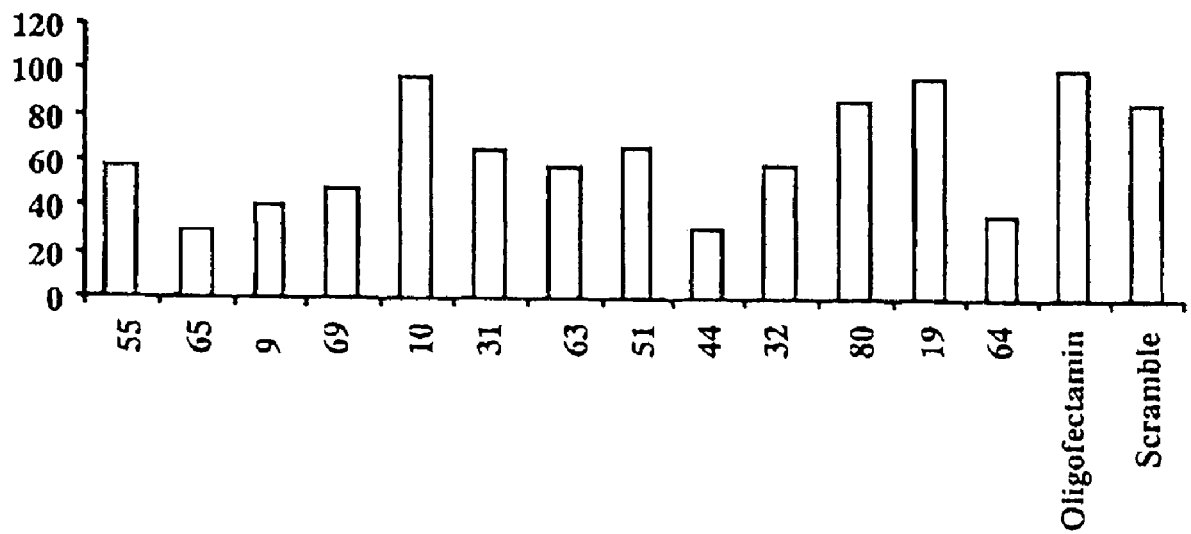
Figure 1E:
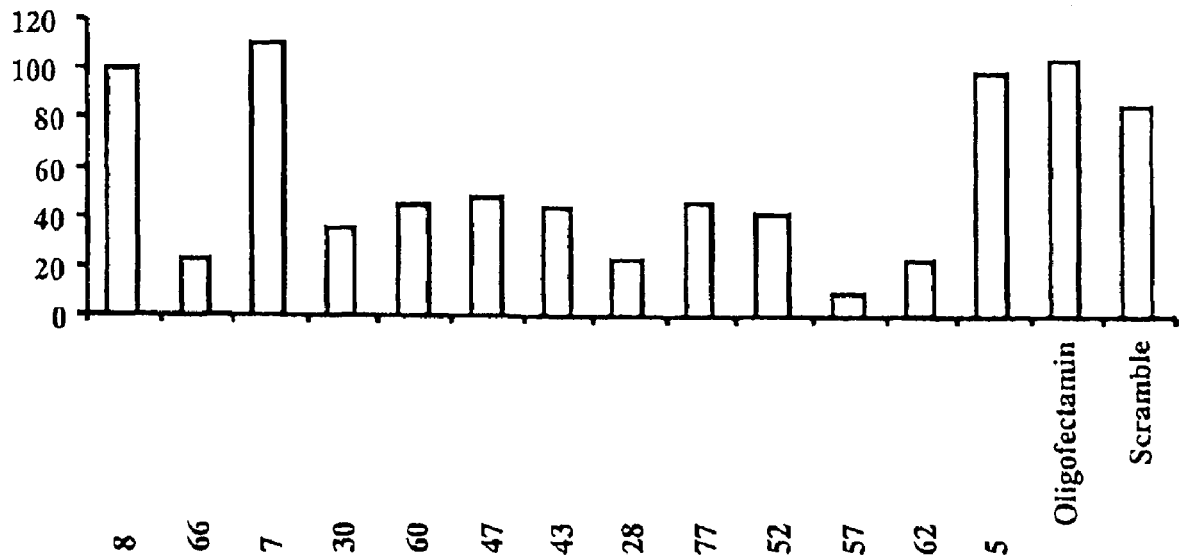
Figure 1F:
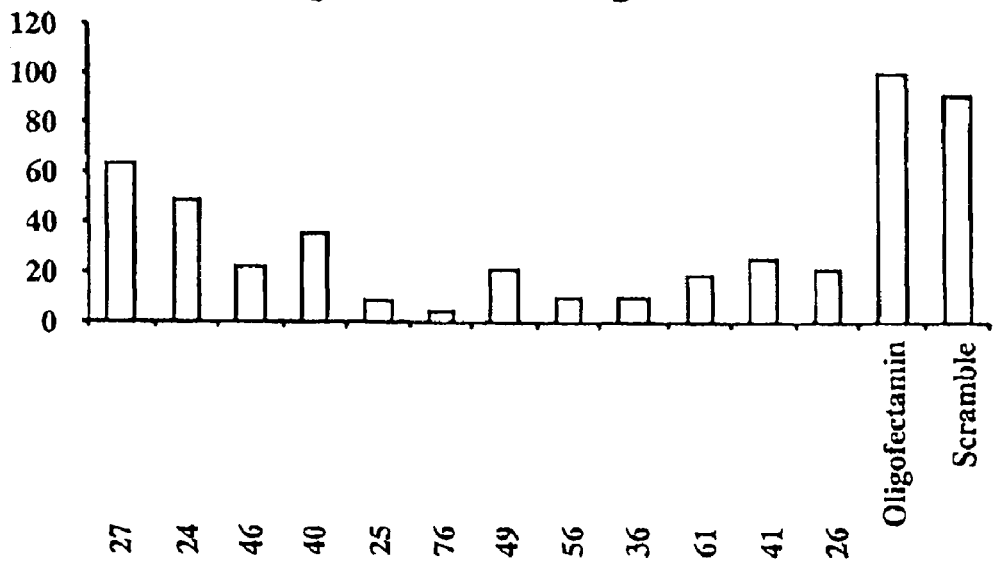
Figure 1G:
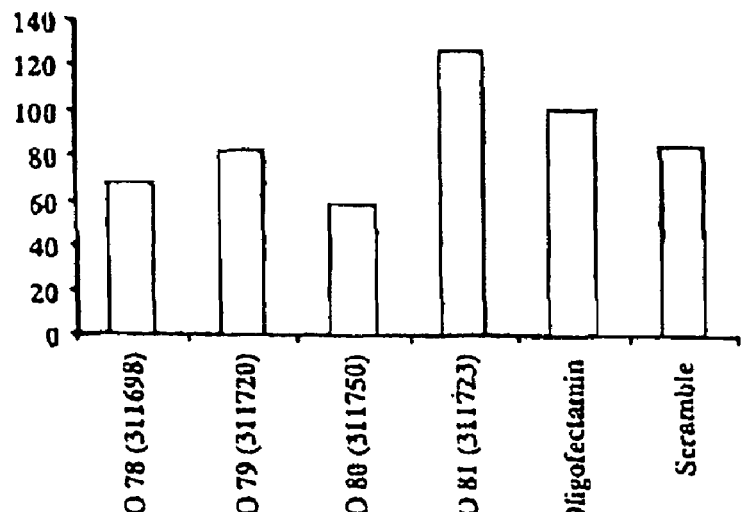

The present invention relates to compositions that reduce the effective amount of active hsp27 in vivo. Exemplary compositions useful in the invention are antisense hsp27 oligonucleotides or RNAi nucleotide inhibitors. The invention further relates to the use of these compositions in the treatment of prostate cancer and other cancers that express hsp27 in elevated amounts.

As used in the specification and claims of this application, the term "active hsp27" refers to hsp27 which is active as a chaperone to stabilize protein structure at times of stress and in particular inhibits the activity of caspase-3, a mediator of apoptosis. Reduction in levels of active hsp27 can be achieved by reducing the total amount of hsp27, either by restricting production of hsp27 or by degrading hsp27 at a rate faster than it is being produced, by converting hsp27 to an inactive form, for example by sequestering hsp27 in an inactive complex such as with an anti-hsp27 antibody.

As used in the specification and claims hereof, the cancers which may be treated are those that express hsp27 in an elevated amounts compared to non-cancerous cells of the same tissue type. Exemplary cancers include without limitation prostate, bladder, lung, breast, osteosarcoma, pancreatic, colon, melanoma, testicular, colorectal, urothelial, renal cell, hepatocellular, leukemia, lymphoma, and ovarian cancer and central nervous system malignancies.

As used in the specification and claims hereof, the term "sequence specificity" refers to the existence of a complementary relationship, using Watson-Crick base pairing, between the oligonucleotide and the hsp27 target that is sufficient to yield specific binding under intra-cellular conditions. Perfect complementarity is desirable, but is not absolutely required, particularly where longer oligonucleotides are employed.

The sequence of human hsp27 mRNA is known, for example from NCBI Accession Numbers AB020027, X54079, NM_006308, NM_001540 and NM_001541. The cDNA sequence (Seq. ID No. 91) forms the basis for the development of antisense oligonucleotides and RNAi nucleotide inhibitors. The preferred sequences for antisense, and for RNAi are those that target bases in the regions from nucleotides 131-161, 241-261, 361-371, 551-580, 661-681 and 744-764 in Seq. ID No. 91. IN order to target bases within these regions, an antisense or RNAi molecule must have sequence specificity with a region that includes at least one of the listed bases, preferably at least 10 of the listed bases.

Suitable antisense oligonucleotides have a length of from 12 to 35 oligonucleotides and have sequence specificity to the hsp27 mRNA sequence. Antisense oligonucleotides that were made and tested for their ability to reduce the amount of active hsp27 mRNA are set forth as Seq ID Nos. 1 to 82. Preferred antisense oligonucleotides have the sequence 5'-ggggacgcg-gcgctcggtcat-3' (Seq. ID No. 81) or 5'-gggacgcggcgctcggtcat-3' (Seq. ID No. 82) which targets the translation initiation site of hsp27 mRNA, as well as those with Seq. ID Nos. 25, 36, 56, 57, 67 and 76.

RNA interference or "RNAi" is a term initially coined by Fire and co-workers to describe the observation that double-stranded RNA (dsRNA) can block gene expression when it is introduced into worms (Fire et al. (1998) Nature 391, 806-811, incorporated herein by reference). dsRNA directs gene-specific, post-transcriptional silencing in many organisms, including vertebrates, and has provided a new tool for studying gene function. RNAi involves mRNA degradation, but many of the biochemical mechanisms underlying this interference are unknown. The use of RNAi has been further described in Carthew et al. (2001) Current Opinions in Cell Biology 13, 244-248, and Elbashir et al. (2001) Nature 411, 494-498, both of which are incorporated herein by reference. The RNAi molecules of the invention are double-stranded or single-stranded RNA of from about 21 to about 23 nucleotides which mediate RNA inhibition. That is, the isolated RNAi of the present invention mediate degradation of mRNA of the hsp27 gene.

The terms RNA, RNA molecule(s), RNA segment(s) and RNA fragment(s) may be used interchangeably to refer to RNA that mediates RNA interference. These terms include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise non-standard nucleotides, including non-naturally occurring nucleotides or deoxyribonucleotides. Collectively, all such altered RNAi compounds are referred to as analogs or analogs of naturally-occurring RNA. RNA of the present invention need only be sufficiently similar to natural RNA that it has the ability to mediate RNAi. As used herein the phrase "mediate RNAi" refers to and indicates the ability to distinguish which mRNA are to be affected by the RNAi machinery or process. RNA that mediates RNAi interacts with the RNAi machinery such that it directs the machinery to degrade particular mRNAs or to otherwise reduce the expression of the target protein. In one embodiment, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or lack of expression of the target mRNA.

As noted above, the RNA molecules of the present invention in general comprise an RNA portion and some additional portion, for example a deoxyribonucleotide portion. The total number of nucleotides in the RNA molecule is suitably less than 49 in order to be effective mediators of RNAi. In preferred RNA molecules, the number of nucleotides is 16 to 29, more preferably 18 to 23, and most preferably 21-23.

The RNA portion of suitable RNAi molecules are set forth in Seq. ID Nos. 83-90. These sequences are the sense RNA strand. They may be used in RNAi treatment in combination with a corresponding antisense strand.

The oligonucleotides employed as antisense or RNAi molecules may be modified to increase the stability of the oligonucleotides in vivo. For example, the oligonucleotides may be employed as phosphorothioate derivatives (replacement of a non-bridging phosphoryl oxygen atoms with a sulfur atom) which have increased resistance to nuclease digestion. MOE modification (ISIS backbone) is also effective.

Administration of antisense oligonucleotides can be carried out using the various mechanisms known in the art, including naked administration and administration in pharmaceutically acceptable lipid carriers. For example, lipid carriers for antisense delivery are disclosed in U.S. Pat. Nos. 5,855,911 and 5,417,978 which are incorporated herein by reference. In general, the antisense is administered by intravenous, intraperitoneal, subcutaneous or oral routes, or direct local tumor injection.

The amount of antisense oligonucleotide or other therapeutic administered is one effective to reduce the amount of active hsp 27. It will be appreciated that this amount will vary both with the effectiveness of the antisense oligonucleotides or other therapeutic agent employed, and with the nature of any carrier used. The determination of appropriate amounts for any given composition is within the skill in the art, through standard series of tests designed to assess appropriate therapeutic levels.

The RNAi molecules of the invention are used in therapy to treat patients, including human patients, that have cancers or other diseases of a type where a therapeutic benefit is obtained by the inhibition of expression of the targeted protein. siRNA molecules of the invention are administered to patients orally, by one or more daily injections (intravenous, subcutaneous, intravesical, or intrathecal) or by continuous intravenous or intrathecal administration for one or more treatment cycles to reach plasma and tissue concentrations suitable for the regulation of the targeted mRNA and protein.

Figure 9:
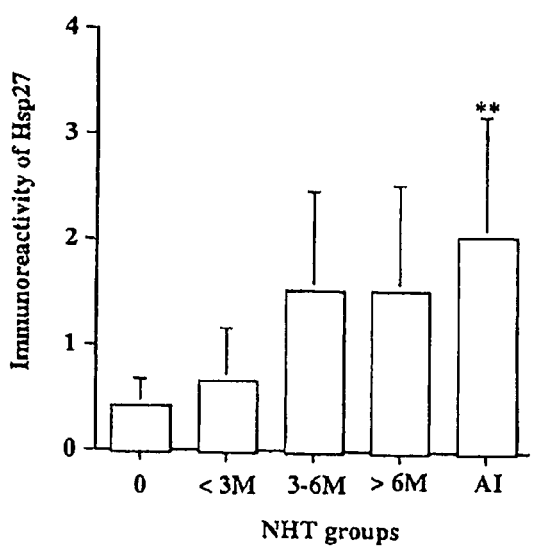
FIG. 9 shows immunoreactivity of hsp27 determined from immunohistological evaluation of hsp27 in an NHT tissue array.

Prostate cancer is one cancer that overexpresses hsp27 in later stage cancers, and in particular in cancers that have become androgen independent, FIG. 9 shows immunoreactivity of hsp27 determined from immunohistological evaluation of hsp27 in an NHT tissue array. In the benign samples, immunoreactivity is limited to the basal layer. As the duration of neoadjuvant therapy increases, the immunoreactivity increases, with androgen independent tumors showing very strong reactivity. For treatment of prostate cancer, the therapeutic compositions of the invention are suitably administered after initial of androgen withdrawal. Initiation of androgen withdrawal may be accomplished via surgical (removal of both testicles) or medical (drug-induced suppression of testosterone) castration, which is currently indicated for treatment of prostate cancer. Medical castration can be achieved by various regimens, including LHRH agents or antiandrogens. (Gleave et al., *CMAJ* 160: 225-232 (1999)). Intermittent therapy in which reversible androgen withdrawal is effected is described in Gleave et al. *Eur. Urol.* 34 (Supp. 3): 37-41 (1998).

The inhibition of hsp 27 expression may be transient, and for treatment of prostate cancer ideally should occur coincident with androgen withdrawal. In humans, this means that inhibition of expression should be effective starting within a day or two of androgen withdrawal (before or after) and extending for about 3 to 6 months. This may require multiple doses to accomplish. It will be appreciated, however, that the period of time may be more prolonged, starting before castration and expending for substantial time afterwards without departing from the scope of the invention.

The method for treating cancer, including prostate cancer, in accordance with the invention may further include administration of chemotherapy agents and/or additional antisense oligonucleotides directed at different targets. Examples of other therapy agents include, without limitation, taxanes (paclitaxel or docetaxel), mitoxanthrone, and antisense directed to Bcl-2, Bcl-xl or c-myc. Inhibition of hsp27 using antisense or RNAi can be used to enhance the activity of like taxanes or gemcitabine, as well as biologic agents for the treatment of prostate, breast, lung, urothelial and other cancers.

The invention will now be further described with respect to the following non-limiting examples.

Example 1

A plurality of antisense compounds as defined in Seq. ID Nos. 1 81 were prepared, and each sequence was tested for levels of Hsp 27 mRNA expression human prostate cancer PC3 cells by Northern Blot after exposure to 50 nM of a specified antisense oligonucleotide in an Oligofectamine carrier. The results of these tests, as a percentage of an Oligofectamine only control, for Seq. ID Nos. 1-81 are shown in FIGS. 1A-G. As shown, although not all antisense sequences are effective, effective antisense sequences are found throughout the length of the hsp27 mRNA.

Example 2

Figure 2:
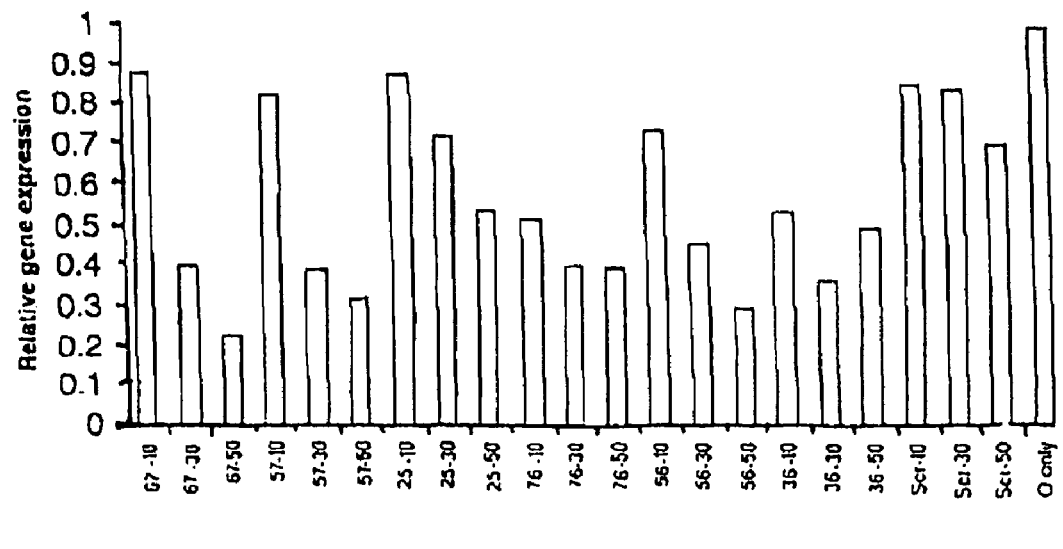
FIG. 2 shows the effect of hsp27 antisense on hsp27 expression in PC3 cells.

PC3 prostate cancer cells were transfected at 40% confluency with three concentrations (10, 30 and 50 nM) of 6 different hsp27-antisense oligonucleotides 2 times, successively in 10 cm dishes, using an Oligofectamine carrier. RNA was extracted 48 hours after the first treatment and analyzed by Northern Blot. The antisense oligonucleotides tested were those with Seq. ID Nos. 67, 57, 25, 76, 56 and 36. As controls, a scrambled oligonucleotide and Oligofectamine only experiments were conducted. All of the oligonucleotides tested showed down-regulation of hsp27 with respect to the controls at least at one of the concentrations. Seqs. ID 71 and 74 appeared to be most effective, with significant down-regulation at 10 nM. The results, relative to a GAPDH control are depicted graphically in FIG. 2.

Example 3

Figure 3A:
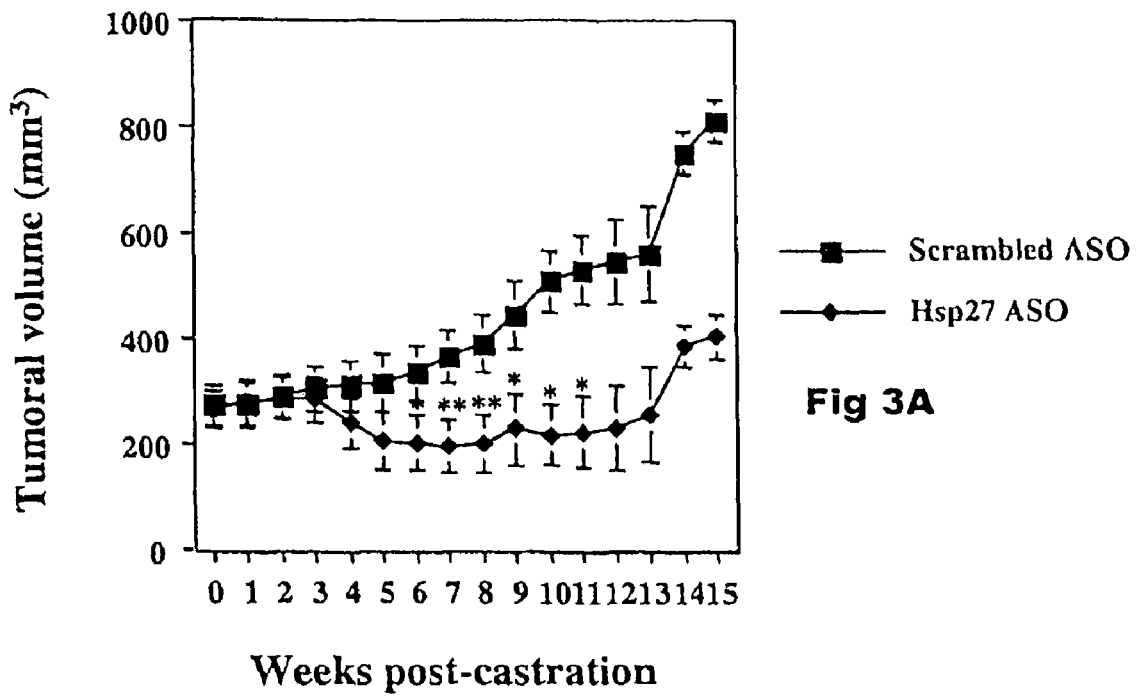
FIGS. 3A and 3B show tumoral volume and serum PSA after treatment with hsp27 antisense.
Figure 3B:
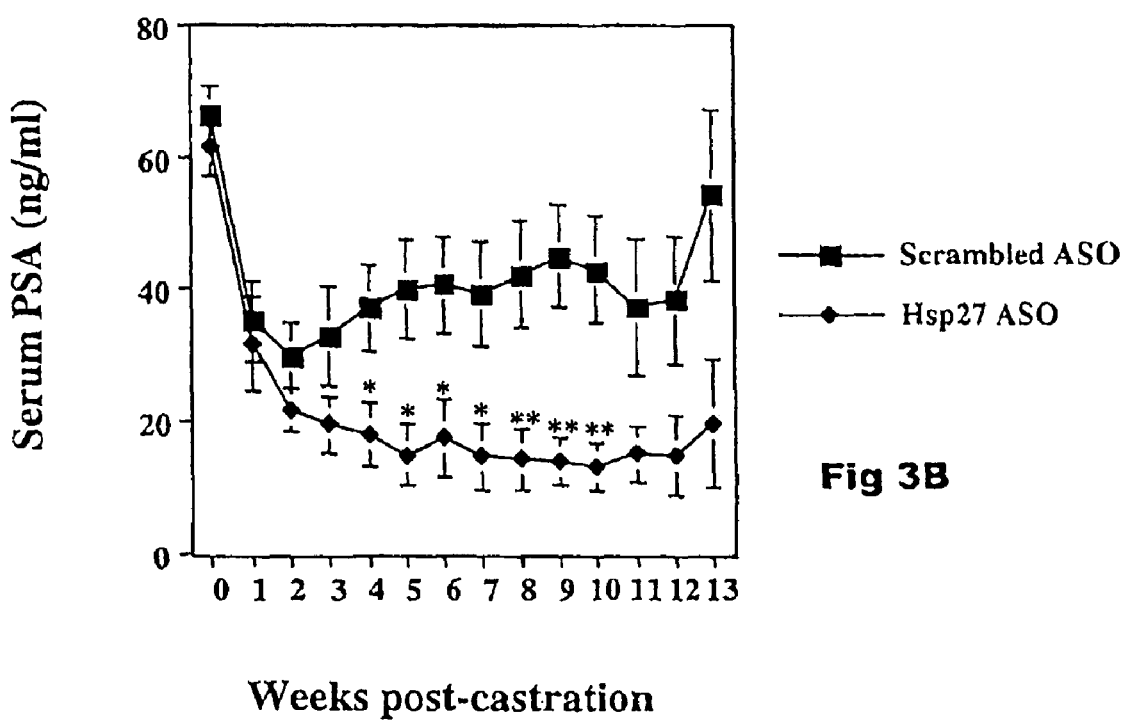

Xenografts of LNCaP prostate cancer cells were introduced into mice, and the effect of intraperitoneal injection of hsp27-antisense oligonucleotide (Seq. ID No. 82) administered intraperitoneally, 10 mg/kg., once daily for four weeks following androgen withdrawal by castration was evaluated. As shown in FIGS. 3A and 3B, tumoral volume and serum PSA increased in the weeks following treatment with a scrambled control, indicating progression to androgen independence, and thus, the loss of efficacy of the castration therapy. In contrast, this progression to androgen independence was not observed in the same time period when treatment with the hsp27 antisense oligonucleotide was given.

Example 4

Figure 4A:
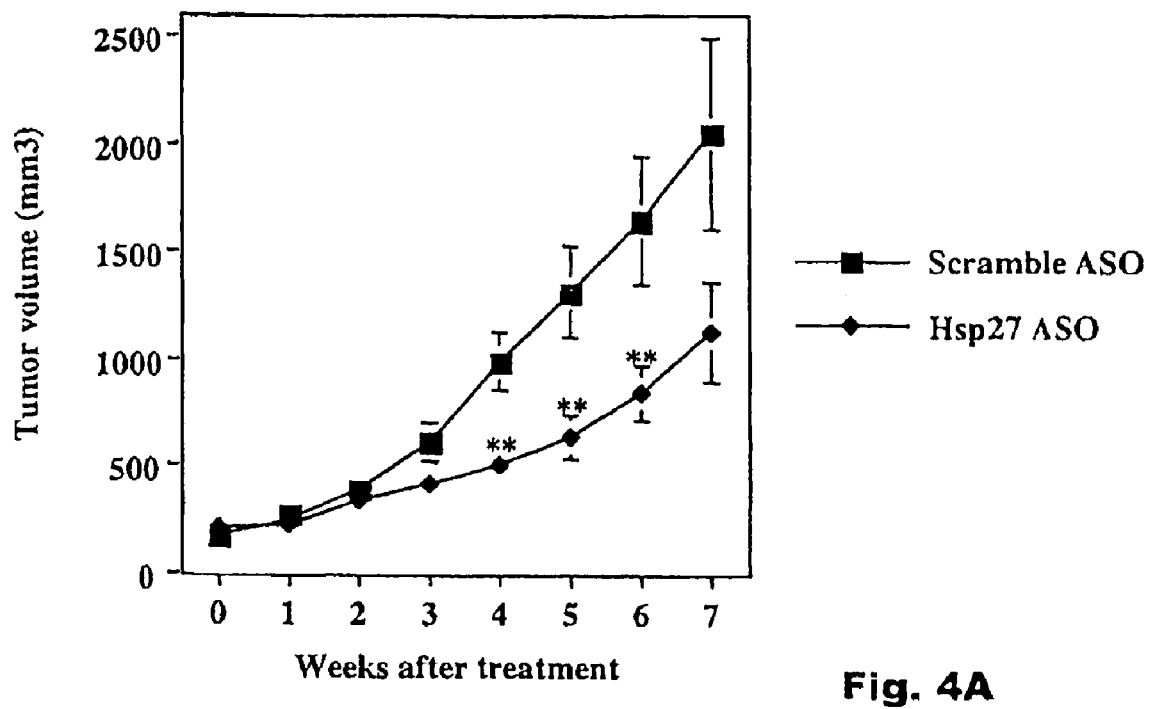
FIGS. 4A and 4B show changes in tumor volume following treatment with hsp27 antisense with and without taxol.
Figure 4B:
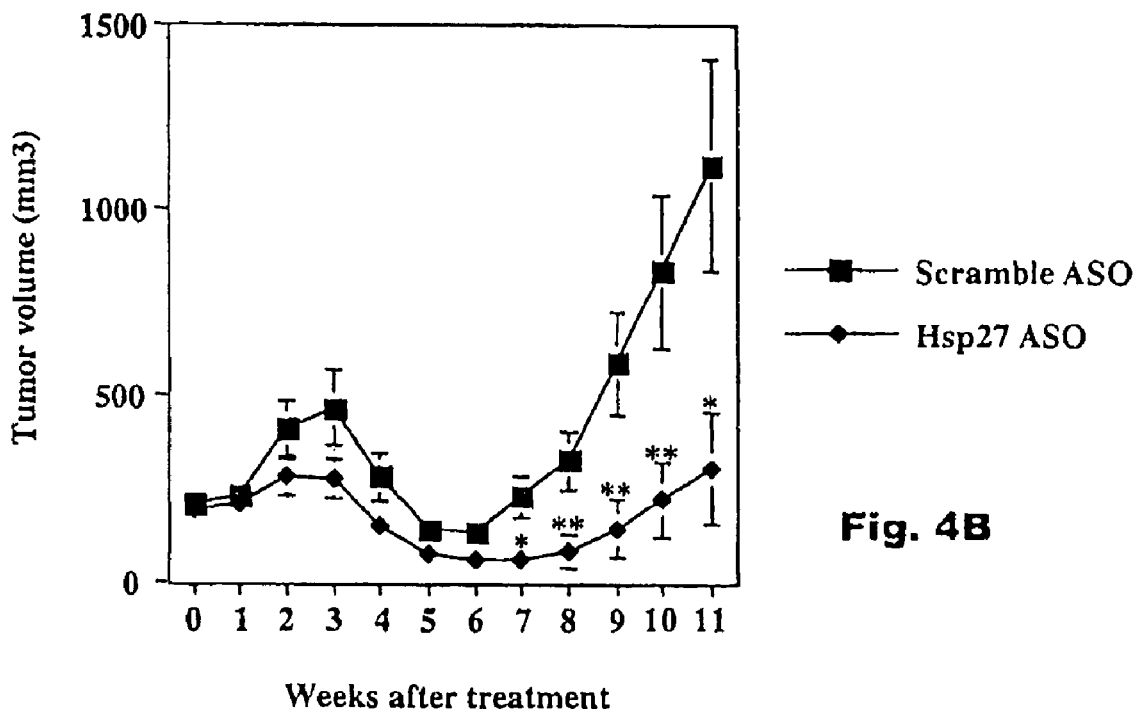

Xenografts of PC3 prostate cancer cells were introduced into mice, and the effect of intraperitoneal injection of hsp27-antisense oligonucleotide (Seq. ID No. 82) administered intraperitoneally, 10 mg/kg., once daily for four weeks with and without Taxol was evaluated. As shown in FIGS. 4A and 4B, tumor volume was significantly reduced by treatment with hsp27-antisense, as compared to scrambled oligonucleotide. This effect was enhanced when taxol treatment was combined with the antisense treatment. FIG. 4A illustrates single agent anti-tumor activity while FIG. 4B illustrates that administration of hsp27 antisense can sensitize cells to paclitaxel in vivo, The control in 4B is scrambled plus taxol.

Example 5

Figure 5:
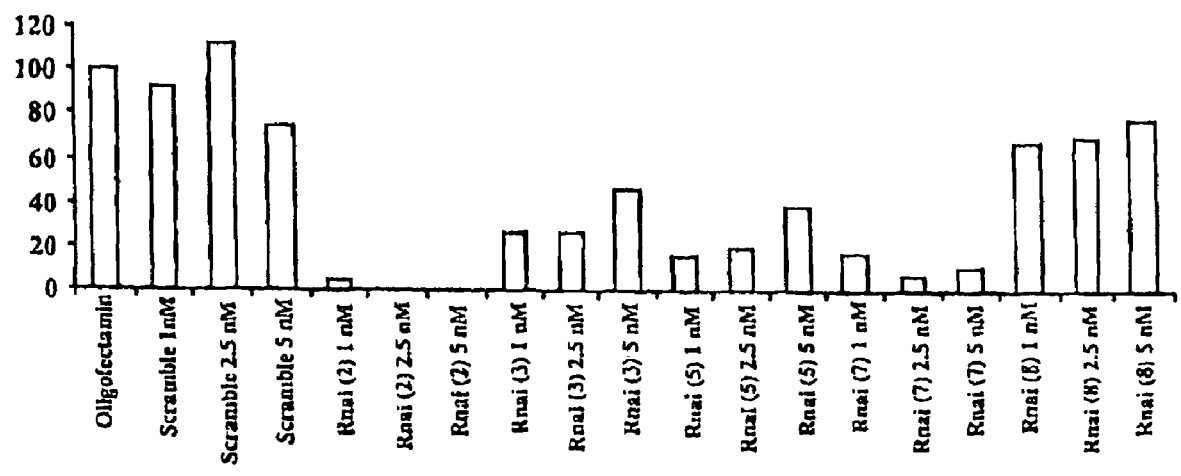
FIG. 5 shows reduction of hsp27 mRNA following treating with RNAi.

RNAi molecules having a sequence in accordance with Seq. ID Nos. 84, 85, 87, 88 and 90 were tested in PC3 cells. The PC cells were transfected with various amounts of the hsp27 siRNA or scrambled control. Two days after transfection, total RNA was extracted and analyzed by Northern blotting for hsp27 and 28S levels. Cells treated with Oligofectimine only were used as an additional control. FIG. 5 shows densitometric measurements of hsp27 mRNA after normalization to 28S mRNA controls. As shown, Seq. ID Nos. 84, 85, 87, 88 and 90 are all effective to significantly reduce hsp27 expression as compared to the scrambled control.

Example 6

Figure 6A:
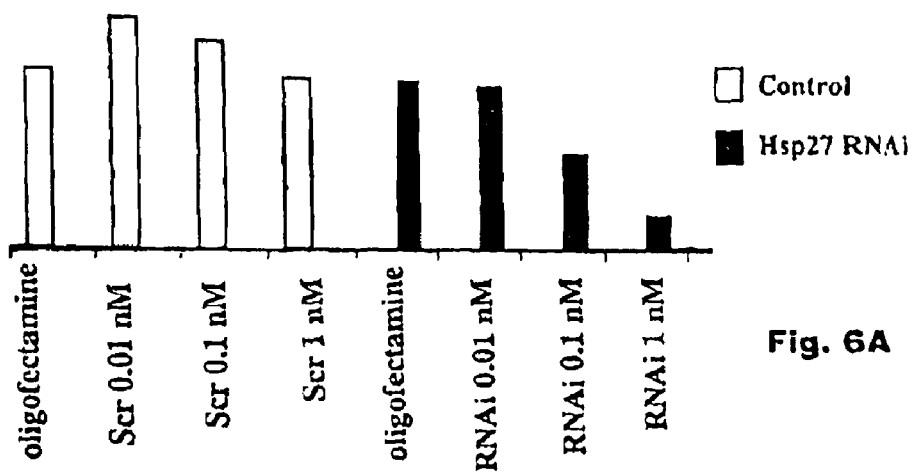
FIGS. 6A and 6B show the amount of expressed hsp27 protein following treatment with RNAi.
Figure 6B:
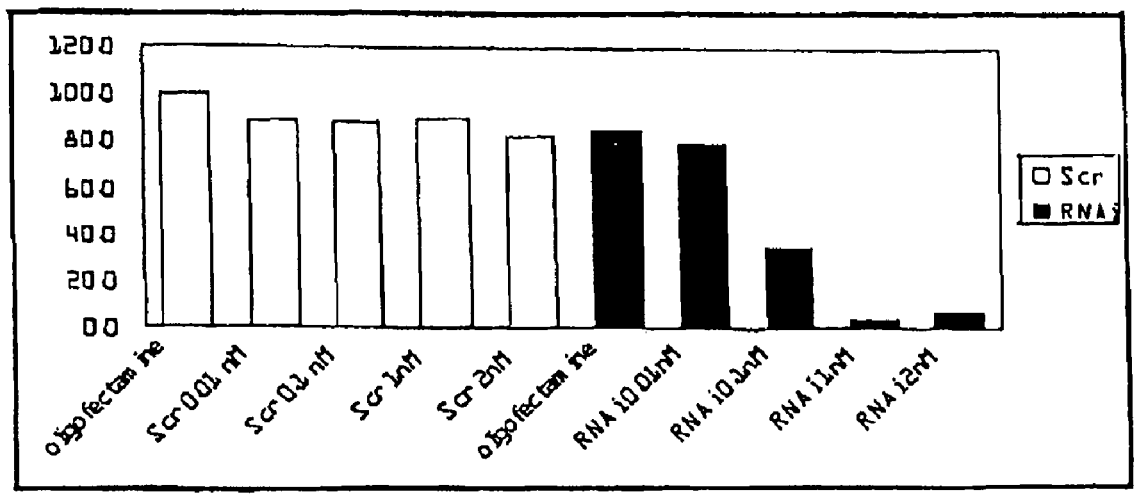

RNAi having a sequence in accordance with Seq ID. No. 84 was transfected into PC3 cells, and the amount of expressed hsp27 protein, as a compared to Vinculin expression was determined. The results are shown in FIGS. 6A and 6B. As shown, a dose dependent reduction in hsp27 expression is observed following treatment with the RNAi molecule.

Example 7

Figure 7A:
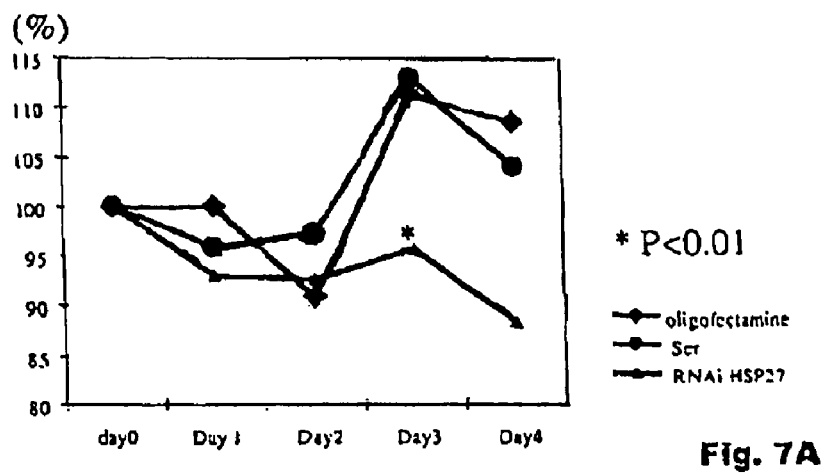
FIGS. 7A-7C shows results of antisense and RNAi treatment of prostate cancer cells.
Figure 7B:
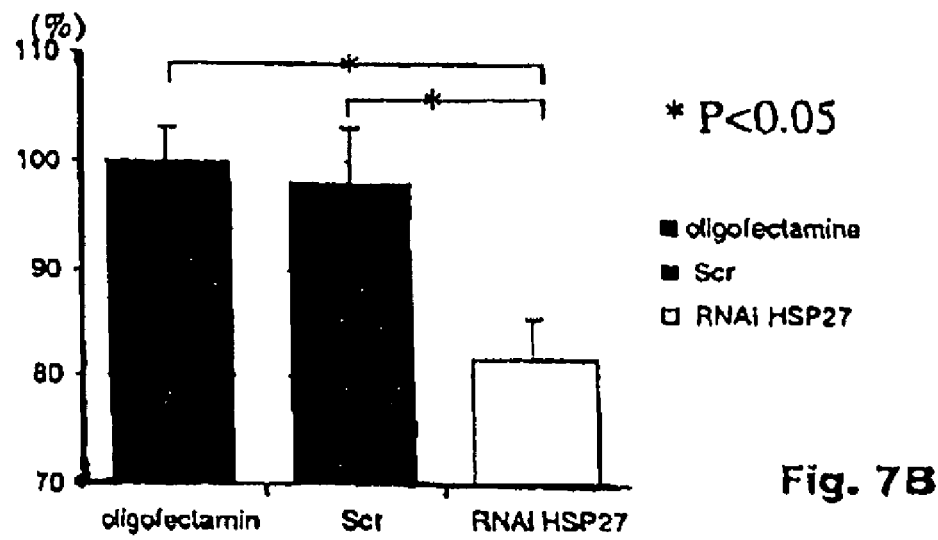
Figure 7C:
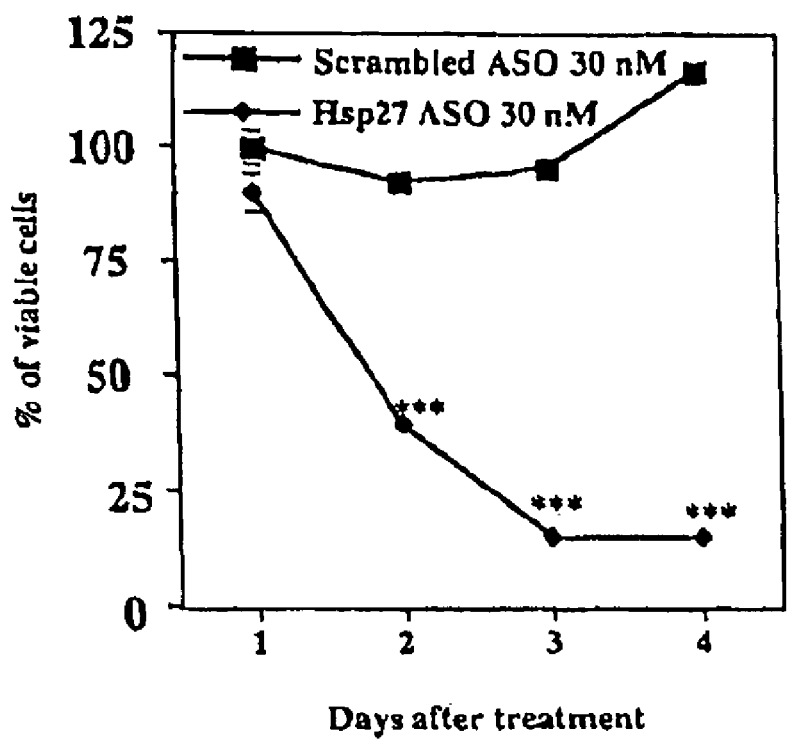

LNCaP cells ($10^4$ cells/well, cultured in 12-well plates) were transfected in vitro with 1 nM RNAi having a sequence in accordance with Seq ID. No. 84. Cell growth was monitored using a Crustal Violet assay. As shown in FIG. 7A, the RNAi treatment resulted in a reduction in cell growth as compared to treatment with Oligofectamine only or a scrambled control. The experiment was repeated using PC3 cells. FIG. 7B shows the % of cells alive 3 days after transfection. FIG. 7C shows growth inhibition of PC3 cells in vitro after treatment with hsp27 antisense Seq, ID NO. 82

Example 8

Figure 8:
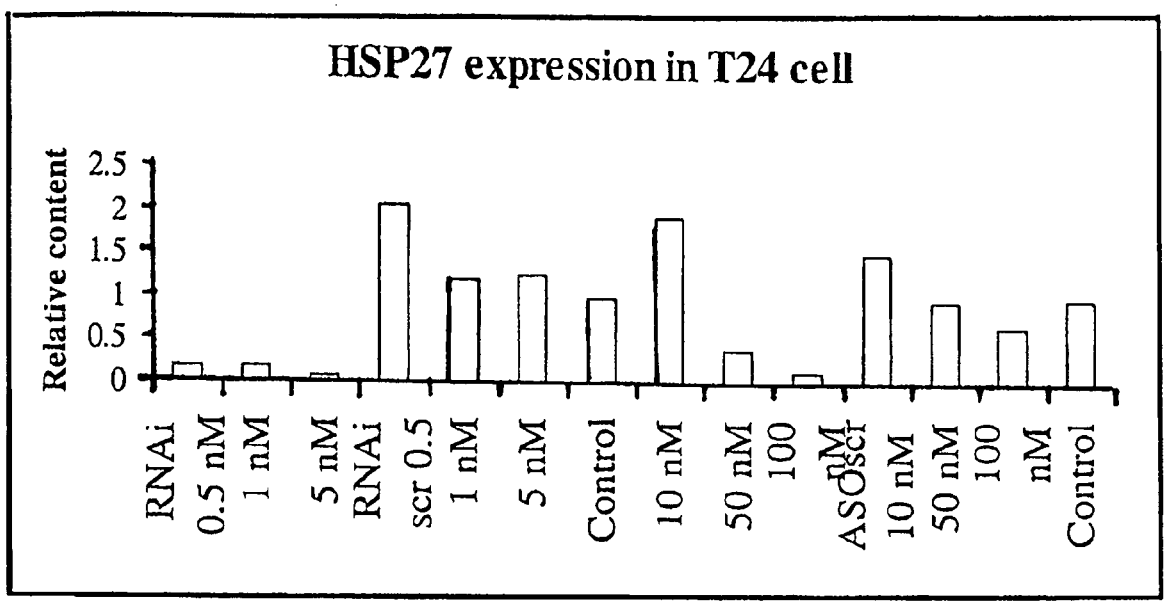
FIG. 8 shows hsp27 expression in T24 bladder cancer cells.

Human bladder cancer T24 cells transfected with hsp27 antisense (Seq. ID No 82) or RNAi (Seq, ID No. 84) were tested for hsp27 expression. As shown in FIG. 8, RNAi and the antisense were both effective to reduce the amount of hsp27 expressed in these cells.

The invention claimed is:

1. A pharmaceutical composition comprising a therapeutic agent effective to reduce the amount of active hsp27 in cancerous cells exposed to the therapeutic agent, and a pharmaceutically acceptable carrier, wherein the therapeutic agent is an antisense oligonucleotide having a sequence complementary to SEQ. ID NO. 91, wherein the oligonucleotide comprises at least ten bases complementary to bases 661-681 of SEQ. ID NO. 91, and wherein the antisense oligonucleotide is 12 to 35 nucleotides in length.

2. The composition of claim 1, wherein the composition is packaged in dosage unit form.

3. The composition of claim 2, wherein the dosage unit form is an injectable solution.

4. The composition of claim 1, wherein the therapeutic agent is an antisense oligonucleotide that comprises the sequence of bases as set forth in SEQ ID NO 66.

5. The composition of claim 4, wherein the composition is packaged in dosage unit form.

6. The composition of claim 5, wherein the dosage unit form is an injectable solution.

7. The composition of claim 1, wherein the therapeutic agent is an antisense oligonucleotide that comprises the sequence of bases as set forth in SEQ. ID NO. 67.

8. The composition of claim 7, wherein the composition is packaged in dosage unit form.

9. The composition of claim 8, wherein the dosage unit form is an injectable solution.

10. The composition of claim 1, wherein the therapeutic agent is an antisense oligonucleotide that comprises the sequence of bases as set forth in SEQ ID NO 68.

11. The composition of claim 10, wherein the composition is packaged in dosage unit form.

12. The composition of claim 11, wherein the dosage unit form is an injectable solution.

13. The composition of claim 1, wherein the therapeutic agent is modified to increase the stability of the oligonucleotide in vivo.

14. The composition of claim 13, wherein the therapeutic agent is a phosphorothioate derivative.

15. The composition of claim 1, wherein the therapeutic agent is an oligodeoxynucleotide.

16. The composition of claim 15, wherein the therapeutic agent is an antisense oligonucleotide that consists of the sequence of bases as set forth in SEQ. ID NO. 67.

17. The composition of claim 15, wherein the therapeutic agent is an antisense oligonucleotide that consists of the sequence of bases as set forth in SEQ. ID NO. 66.

18. The composition of claim 15, wherein the therapeutic agent is an antisense oligonucleotide that consists of the sequence of bases as set forth in SEQ. ID NO. 66.

* * * * *

SEQUENCE LISTING

<160> NUMBER OF SEQ ID NOS: 91

<210> SEQ ID NO 1
<211> LENGTH: 21
<212> TYPE: DNA

-continued

<213> ORGANISM: Homo sapiens

<400> SEQUENCE: 1
gctgactctg ctcctcgtgc c                                              21

<210> SEQ ID NO 2
<211> LENGTH: 21
<212> TYPE: DNA
<213> ORGANISM: Homo sapiens

<400> SEQUENCE: 2
ggtcatgctg gctgactctg c                                              21

<210> SEQ ID NO 3
<211> LENGTH: 21
<212> TYPE: DNA
<213> ORGANISM: Homo sapiens

<400> SEQUENCE: 3
cgcggcgctc ggtcatgctg g                                              21

<210> SEQ ID NO 4
<211> LENGTH: 21
<212> TYPE: DNA
<213> ORGANISM: Homo sapiens

<400> SEQUENCE: 4
gagaagggga cgcggcgctc g                                              21

<210> SEQ ID NO 5
<211> LENGTH: 21
<212> TYPE: DNA
<213> ORGANISM: Homo sapiens

<400> SEQUENCE: 5
ccgcaggagc gagaagggga c                                              21

<210> SEQ ID NO 6
<211> LENGTH: 21
<212> TYPE: DNA
<213> ORGANISM: Homo sapiens

<400> SEQUENCE: 6
agctggggcc ccgcaggagc g                                              21

<210> SEQ ID NO 7
<211> LENGTH: 21
<212> TYPE: DNA
<213> ORGANISM: Homo sapiens

<400> SEQUENCE: 7
aaggggtccc agctggggcc c                                              21

<210> SEQ ID NO 8
<211> LENGTH: 21
<212> TYPE: DNA
<213> ORGANISM: Homo sapiens

<400> SEQUENCE: 8
ccagtcgcgg aaggggtccc a                                              21

<210> SEQ ID NO 9
<211> LENGTH: 21

```
<212> TYPE: DNA
<213> ORGANISM: Homo sapiens

<400> SEQUENCE: 9
tatgcgggta ccagtcgcgg a                                              21

<210> SEQ ID NO 10
<211> LENGTH: 21
<212> TYPE: DNA
<213> ORGANISM: Homo sapiens

<400> SEQUENCE: 10
aagaggcggc tatgcgggta c                                              21

<210> SEQ ID NO 11
<211> LENGTH: 21
<212> TYPE: DNA
<213> ORGANISM: Homo sapiens

<400> SEQUENCE: 11
ggcctggtcg aagaggcggc t                                              21

<210> SEQ ID NO 12
<211> LENGTH: 21
<212> TYPE: DNA
<213> ORGANISM: Homo sapiens

<400> SEQUENCE: 12
gcagcccgaa ggcctggtcg a                                              21

<210> SEQ ID NO 13
<211> LENGTH: 21
<212> TYPE: DNA
<213> ORGANISM: Homo sapiens

<400> SEQUENCE: 13
ggcagccggg gcagcccgaa g                                              21

<210> SEQ ID NO 14
<211> LENGTH: 21
<212> TYPE: DNA
<213> ORGANISM: Homo sapiens

<400> SEQUENCE: 14
ccactcctcc ggcagccggg g                                              21

<210> SEQ ID NO 15
<211> LENGTH: 21
<212> TYPE: DNA
<213> ORGANISM: Homo sapiens

<400> SEQUENCE: 15
accactgcga ccactcctcc g                                              21

<210> SEQ ID NO 16
<211> LENGTH: 21
<212> TYPE: DNA
<213> ORGANISM: Homo sapiens

<400> SEQUENCE: 16
ctgccgccta accactgcga c                                              21

<210> SEQ ID NO 17
```

```
<211> LENGTH: 21
<212> TYPE: DNA
<213> ORGANISM: Homo sapiens

<400> SEQUENCE: 17
tggccagctg ctgccgccta a                                              21

<210> SEQ ID NO 18
<211> LENGTH: 21
<212> TYPE: DNA
<213> ORGANISM: Homo sapiens

<400> SEQUENCE: 18
gcacgtagcc tggccagctg c                                              21

<210> SEQ ID NO 19
<211> LENGTH: 21
<212> TYPE: DNA
<213> ORGANISM: Homo sapiens

<400> SEQUENCE: 19 ggcaggggggc gcacgtagcc t                                             21

<210> SEQ ID NO 20
<211> LENGTH: 21
<212> TYPE: DNA
<213> ORGANISM: Homo sapiens

<400> SEQUENCE: 20
ggcggcgggg ggcaggggggc g                                             21

<210> SEQ ID NO 21
<211> LENGTH: 21
<212> TYPE: DNA
<213> ORGANISM: Homo sapiens

<400> SEQUENCE: 21
ggctctcgat ggcggcgggg g                                              21

<210> SEQ ID NO 22
<211> LENGTH: 21
<212> TYPE: DNA
<213> ORGANISM: Homo sapiens

<400> SEQUENCE: 22
gccactgcgg ggctctcgat g                                              21

<210> SEQ ID NO 23
<211> LENGTH: 21
<212> TYPE: DNA
<213> ORGANISM: Homo sapiens

<400> SEQUENCE: 23
ggcgggcgcg gccactgcgg g                                              21

<210> SEQ ID NO 24
<211> LENGTH: 21
<212> TYPE: DNA
<213> ORGANISM: Homo sapiens

<400> SEQUENCE: 24
cgcggctgta ggcgggcgcg g                                              21
```

```
<210> SEQ ID NO 25
<211> LENGTH: 21
<212> TYPE: DNA
<213> ORGANISM: Homo sapiens

<400> SEQUENCE: 25
cggctgagcg cgcggctgta g                                      21

<210> SEQ ID NO 26
<211> LENGTH: 21
<212> TYPE: DNA
<213> ORGANISM: Homo sapiens

<400> SEQUENCE: 26
gctgagttgc cggctgagcg c                                      21

<210> SEQ ID NO 27
<211> LENGTH: 21
<212> TYPE: DNA
<213> ORGANISM: Homo sapiens

<400> SEQUENCE: 27
agaccccgct gctgagttgc c                                      21

<210> SEQ ID NO 28
<211> LENGTH: 21
<212> TYPE: DNA
<213> ORGANISM: Homo sapiens

<400> SEQUENCE: 28
cggatctccg agaccccgct g                                      21

<210> SEQ ID NO 29
<211> LENGTH: 21
<212> TYPE: DNA
<213> ORGANISM: Homo sapiens

<400> SEQUENCE: 29
cgcagtgtgc cggatctccg a                                      21

<210> SEQ ID NO 30
<211> LENGTH: 21
<212> TYPE: DNA
<213> ORGANISM: Homo sapiens

<400> SEQUENCE: 30
gccagcggtc cgcagtgtgc c                                      21

<210> SEQ ID NO 31
<211> LENGTH: 21
<212> TYPE: DNA
<213> ORGANISM: Homo sapiens

<400> SEQUENCE: 31
agggacacgc gccagcggtc c                                      21

<210> SEQ ID NO 32
<211> LENGTH: 21
<212> TYPE: DNA
<213> ORGANISM: Homo sapiens

<400> SEQUENCE: 32
gttgacatcc agggacacgc g                                      21
```

```
<210> SEQ ID NO 33
<211> LENGTH: 21
<212> TYPE: DNA
<213> ORGANISM: Homo sapiens

<400> SEQUENCE: 33
gggcgaagtg gttgacatcc a                                              21

<210> SEQ ID NO 34
<211> LENGTH: 21
<212> TYPE: DNA
<213> ORGANISM: Homo sapiens

<400> SEQUENCE: 34
agctcgtccg gggcgaagtg g                                              21

<210> SEQ ID NO 35
<211> LENGTH: 21
<212> TYPE: DNA
<213> ORGANISM: Homo sapiens

<400> SEQUENCE: 35
cttgaccgtc agctcgtccg g                                              21

<210> SEQ ID NO 36
<211> LENGTH: 21
<212> TYPE: DNA
<213> ORGANISM: Homo sapiens

<400> SEQUENCE: 36
catccttggt cttgaccgtc a                                              21

<210> SEQ ID NO 37
<211> LENGTH: 21
<212> TYPE: DNA
<213> ORGANISM: Homo sapiens

<400> SEQUENCE: 37
tccaccacgc catccttggt c                                              21

<210> SEQ ID NO 38
<211> LENGTH: 21
<212> TYPE: DNA
<213> ORGANISM: Homo sapiens

<400> SEQUENCE: 38
gccggtgatc tccaccacgc c                                              21

<210> SEQ ID NO 39
<211> LENGTH: 21
<212> TYPE: DNA
<213> ORGANISM: Homo sapiens

<400> SEQUENCE: 39
cctcgtgctt gccggtgatc t                                              21

<210> SEQ ID NO 40
<211> LENGTH: 21
<212> TYPE: DNA
<213> ORGANISM: Homo sapiens

<400> SEQUENCE: 40
tcctgccgct cctcgtgctt g                                              21
```

-continued

```
<210> SEQ ID NO 41
<211> LENGTH: 21
<212> TYPE: DNA
<213> ORGANISM: Homo sapiens

<400> SEQUENCE: 41
gccatgctcg tcctgccgct c                                              21

<210> SEQ ID NO 42
<211> LENGTH: 21
<212> TYPE: DNA
<213> ORGANISM: Homo sapiens

<400> SEQUENCE: 42
gggagatgta gccatgctcg t                                              21

<210> SEQ ID NO 43
<211> LENGTH: 21
<212> TYPE: DNA
<213> ORGANISM: Homo sapiens

<400> SEQUENCE: 43
gtgaagcacc gggagatgta g                                              21

<210> SEQ ID NO 44
<211> LENGTH: 21
<212> TYPE: DNA
<213> ORGANISM: Homo sapiens

<400> SEQUENCE: 44
gtatttccgc gtgaagcacc g                                              21

<210> SEQ ID NO 45
<211> LENGTH: 21
<212> TYPE: DNA
<213> ORGANISM: Homo sapiens

<400> SEQUENCE: 45
ggggcagcgt gtatttccgc g                                              21

<210> SEQ ID NO 46
<211> LENGTH: 21
<212> TYPE: DNA
<213> ORGANISM: Homo sapiens

<400> SEQUENCE: 46
tccacaccgg ggggcagcgt g                                              21

<210> SEQ ID NO 47
<211> LENGTH: 21
<212> TYPE: DNA
<213> ORGANISM: Homo sapiens

<400> SEQUENCE: 47
ttgggtgggg tccacaccgg g                                              21

<210> SEQ ID NO 48
<211> LENGTH: 21
<212> TYPE: DNA
<213> ORGANISM: Homo sapiens

<400> SEQUENCE: 48
```
aggaggaaac ttgggtgggg t         21

<210> SEQ ID NO 49
<211> LENGTH: 21
<212> TYPE: DNA
<213> ORGANISM: Homo sapiens

<400> SEQUENCE: 49
ggggacaggg aggaggaaac t         21

<210> SEQ ID NO 50
<211> LENGTH: 21
<212> TYPE: DNA
<213> ORGANISM: Homo sapiens

<400> SEQUENCE: 50
tgtgccctca ggggacaggg a         21

<210> SEQ ID NO 51
<211> LENGTH: 21
<212> TYPE: DNA
<213> ORGANISM: Homo sapiens

<400> SEQUENCE: 51
ccacggtcag tgtgccctca g         21

<210> SEQ ID NO 52
<211> LENGTH: 21
<212> TYPE: DNA
<213> ORGANISM: Homo sapiens

<400> SEQUENCE: 52
atgggggcct ccacggtcag t         21

<210> SEQ ID NO 53
<211> LENGTH: 21
<212> TYPE: DNA
<213> ORGANISM: Homo sapiens

<400> SEQUENCE: 53
tagcttgggc atgggggcct c         21

<210> SEQ ID NO 54
<211> LENGTH: 21
<212> TYPE: DNA
<213> ORGANISM: Homo sapiens

<400> SEQUENCE: 54
actgcgtggc tagcttgggc a         21

<210> SEQ ID NO 55
<211> LENGTH: 21
<212> TYPE: DNA
<213> ORGANISM: Homo sapiens

<400> SEQUENCE: 55
atctcgttgg actgcgtggc t         21

<210> SEQ ID NO 56
<211> LENGTH: 21
<212> TYPE: DNA
<213> ORGANISM: Homo sapiens

<400> SEQUENCE: 56

```
tgggatggtg atctcgttgg a                                    21

<210> SEQ ID NO 57
<211> LENGTH: 21
<212> TYPE: DNA
<213> ORGANISM: Homo sapiens

<400> SEQUENCE: 57
cgaaggtgac tgggatggtg a                                    21

<210> SEQ ID NO 58
<211> LENGTH: 21
<212> TYPE: DNA
<213> ORGANISM: Homo sapiens

<400> SEQUENCE: 58
gcccgcgact cgaaggtgac t                                    21

<210> SEQ ID NO 59
<211> LENGTH: 21
<212> TYPE: DNA
<213> ORGANISM: Homo sapiens

<400> SEQUENCE: 59
cccaagctgg gcccgcgact c                                    21

<210> SEQ ID NO 60
<211> LENGTH: 21
<212> TYPE: DNA
<213> ORGANISM: Homo sapiens

<400> SEQUENCE: 60
cttctgggcc cccaagctgg g                                    21

<210> SEQ ID NO 61
<211> LENGTH: 21
<212> TYPE: DNA
<213> ORGANISM: Homo sapiens

<400> SEQUENCE: 61
gattttgcag cttctgggcc c                                    21

<210> SEQ ID NO 62
<211> LENGTH: 21
<212> TYPE: DNA
<213> ORGANISM: Homo sapiens

<400> SEQUENCE: 62
agtctcatcg gattttgcag c                                    21

<210> SEQ ID NO 63
<211> LENGTH: 21
<212> TYPE: DNA
<213> ORGANISM: Homo sapiens

<400> SEQUENCE: 63
acttggcggc agtctcatcg g                                    21

<210> SEQ ID NO 64
<211> LENGTH: 21
<212> TYPE: DNA
<213> ORGANISM: Homo sapiens
```

```
<400> SEQUENCE: 64
ctaaggcttt acttggcggc a                                         21

<210> SEQ ID NO 65
<211> LENGTH: 21
<212> TYPE: DNA
<213> ORGANISM: Homo sapiens

<400> SEQUENCE: 65
ggcatccggg ctaaggcttt a                                         21

<210> SEQ ID NO 66
<211> LENGTH: 21
<212> TYPE: DNA
<213> ORGANISM: Homo sapiens

<400> SEQUENCE: 66 agcagggtg ggcatccggg c                                          21

<210> SEQ ID NO 67
<211> LENGTH: 21
<212> TYPE: DNA
<213> ORGANISM: Homo sapiens

<400> SEQUENCE: 67
cagtggcggc agcagggtg g                                          21

<210> SEQ ID NO 68
<211> LENGTH: 21
<212> TYPE: DNA
<213> ORGANISM: Homo sapiens

<400> SEQUENCE: 68
gaggcacagc cagtggcggc a                                         21

<210> SEQ ID NO 69
<211> LENGTH: 21
<212> TYPE: DNA
<213> ORGANISM: Homo sapiens

<400> SEQUENCE: 69
ggtggcgggg gaggcacagc c                                         21

<210> SEQ ID NO 70
<211> LENGTH: 21
<212> TYPE: DNA
<213> ORGANISM: Homo sapiens

<400> SEQUENCE: 70
agaacacaca ggtggcgggg g                                         21

<210> SEQ ID NO 71
<211> LENGTH: 21
<212> TYPE: DNA
<213> ORGANISM: Homo sapiens

<400> SEQUENCE: 71
atgtatcaaa agaacacaca g                                         21

<210> SEQ ID NO 72
<211> LENGTH: 21
<212> TYPE: DNA
<213> ORGANISM: Homo sapiens
```

```
<400> SEQUENCE: 72
cagaagataa atgtatcaaa a                                              21

<210> SEQ ID NO 73
<211> LENGTH: 21
<212> TYPE: DNA
<213> ORGANISM: Homo sapiens

<400> SEQUENCE: 73
ttgagaaaaa cagaagataa a                                              21

<210> SEQ ID NO 74
<211> LENGTH: 21
<212> TYPE: DNA
<213> ORGANISM: Homo sapiens

<400> SEQUENCE: 74
tgaactttat ttgagaaaaa c                                              21

<210> SEQ ID NO 75
<211> LENGTH: 21
<212> TYPE: DNA
<213> ORGANISM: Homo sapiens

<400> SEQUENCE: 75
gtggttgctt tgaactttat t                                              21

<210> SEQ ID NO 76
<211> LENGTH: 21
<212> TYPE: DNA
<213> ORGANISM: Homo sapiens

<400> SEQUENCE: 76
caggtggttg ctttgaactt t                                              21

<210> SEQ ID NO 77
<211> LENGTH: 18
<212> TYPE: DNA
<213> ORGANISM: Homo sapiens

<400> SEQUENCE: 77
taggcgggcg cggccact                                                  18

<210> SEQ ID NO 78
<211> LENGTH: 21
<212> TYPE: DNA
<213> ORGANISM: Homo sapiens

<400> SEQUENCE: 78
gatctccacc acgccatcct t                                              21

<210> SEQ ID NO 79
<211> LENGTH: 21
<212> TYPE: DNA
<213> ORGANISM: Homo sapiens

<400> SEQUENCE: 79
tccgagaccc cgctgctgag t                                              21

<210> SEQ ID NO 80
<211> LENGTH: 21
<212> TYPE: DNA
```

-continued

<213> ORGANISM: Homo sapiens

<400> SEQUENCE: 80
ccgagacccc gctgctgagt t          21

<210> SEQ ID NO 81
<211> LENGTH: 21
<212> TYPE: DNA
<213> ORGANISM: Homo sapiens

<400> SEQUENCE: 81
ggggacgcgg cgctcggtca t          21

<210> SEQ ID NO 82
<211> LENGTH: 20
<212> TYPE: DNA
<213> ORGANISM: Homo sapiens

<400> SEQUENCE: 82
gggacgcggc gctcggtcat            20

<210> SEQ ID NO 83
<211> LENGTH: 19
<212> TYPE: RNA
<213> ORGANISM: Homo sapiens

<400> SEQUENCE: 83
cucugcugcg ggucucgg              19

<210> SEQ ID NO 84
<211> LENGTH: 20
<212> TYPE: RNA
<213> ORGANISM: Homo sapiens

<400> SEQUENCE: 84
gcugcuuuuu ccguuguguc            20

<210> SEQ ID NO 85
<211> LENGTH: 19
<212> TYPE: RNA
<213> ORGANISM: Homo sapiens

<400> SEQUENCE: 85
gguuggcgug gugguguuc             19

<210> SEQ ID NO 86
<211> LENGTH: 19
<212> TYPE: RNA
<213> ORGANISM: Homo sapiens

<400> SEQUENCE: 86
gcucguggug cggcugguc             19

<210> SEQ ID NO 87
<211> LENGTH: 19
<212> TYPE: RNA
<213> ORGANISM: Homo sapiens

<400> SEQUENCE: 87
cgagaucacc aucccaguc             19

<210> SEQ ID NO 88
<211> LENGTH: 19

```
-continued

<212> TYPE: RNA
<213> ORGANISM: Homo sapiens

<400> SEQUENCE: 88
guucuccuuc ccugucucc                                                    19

<210> SEQ ID NO 89
<211> LENGTH: 21
<212> TYPE: RNA
<213> ORGANISM: Homo sapiens

<400> SEQUENCE: 89
ccuucguguc gcgggcccug c                                                 21

<210> SEQ ID NO 90
<211> LENGTH: 19
<212> TYPE: RNA
<213> ORGANISM: Homo sapiens

<400> SEQUENCE: 90
augaccgagc gccgcgucc                                                    19

<210> SEQ ID NO 91
<211> LENGTH: 764
<212> TYPE: DNA
<213> ORGANISM: Homo sapiens

<400> SEQUENCE: 91
ggcacgagga gcagagtcag ccagcatgac cgagcgccgc gtcccctct cgctcctgcg         60
gggccccagc tgggacccct tccgcgactg gtacccgcat agccgcctct tcgaccaggc       120
cttcgggctg ccccggctgc cggaggagtg gtcgcagtgg ttaggcggca gcagctggcc       180
aggctacgtg cgcccctgc cccccgccgc catcgagagc cccgcagtgg ccgcgcccgc        240
ctacagccgc gcgctcagcc ggcaactcag cagcggggtc tcggagatcc ggcacactgc       300
ggaccgctgg cgcgtgtccc tggatgtcaa ccacttcgcc ccggacgagc tgacggtcaa       360
gaccaaggat ggcgtggtgg agatcaccgg caagcacgag gagcggcagg acgagcatgg       420
ctacatctcc cggtgcttca cgcggaaata cacgctgccc cccggtgtgg accccaccca       480
agtttcctcc tccctgtccc ctgagggcac actgaccgtg gaggccccca tgcccaagct       540
agccacgcag tccaacgaga tcaccatccc agtcaccttc gagtcgcggg cccagcttgg       600
gggcccagaa gctgcaaaat ccgatgagac tgccgcaag taaagcctta gcccggatgc        660
ccacccctgc tgccgccact ggctgtgcct cccccgccac ctgtgtgttc ttttgataca       720
tttatcttct gtttttctca aataaagttc aaagcaacca cctg                       764
```